United States Patent [19]

Behney

[11] 4,252,110
[45] Feb. 24, 1981

[54] EAR IMPLANT ARTICLE AND IMPLANTATION METHOD

[76] Inventor: Charles A. Behney, Box 4337, Bisbee, Ariz. 85603

[21] Appl. No.: 943,568

[22] Filed: Sep. 18, 1978

[51] Int. Cl.³ .............................................. A61B 19/00
[52] U.S. Cl. ...................... 128/1 R; 119/96; 3/1.0; 3/1.9; 128/92 C
[58] Field of Search ...................... 3/1.9, 1.0; 119/96; 128/127, 130, 214.4, 92 C, 1 R; 2/264

[56] References Cited

U.S. PATENT DOCUMENTS

| | | | |
|---|---|---|---|
| 2,644,946 | 7/1953 | Menz et al. | 2/264 |
| 3,425,411 | 2/1969 | Robinson | 128/130 |
| 3,579,831 | 5/1971 | Stevens et al. | 128/92 C |
| 3,678,927 | 7/1972 | Soichet | 128/130 |
| 4,147,164 | 4/1979 | Behney | 3/1 |

FOREIGN PATENT DOCUMENTS

782496  9/1957  United Kingdom ..................... 128/130

OTHER PUBLICATIONS

Arch. Surgury vol. 97 "A Successful Silicone Tendon Prosthesis" Sep. 1968 pp. 406–411.

*Primary Examiner*—William E. Kamm
*Assistant Examiner*—J. L. Kruter
*Attorney, Agent, or Firm*—Gerlach & O'Brien

[57] ABSTRACT

An article of manufacture for use as an implant in the animal ear to correct a faulty carriage of the ear occasioned by the presence of a skin-enclosed cartilage fault comprises a spring constructed of non-porous biologically inert material, the spring having outwardly divergent arms terminating in outer free ends and adapted to be forced together to present a narrow elongated spring outline for implantation of the spring in the ear by insertion through a small incision in the skin of the ear with the free ends foremost and into a pocket previously formed between the skin and cartilage over a cartilage fault, so that the spring bridges the fault, the spring arms when free of applied force tending to return to their original divergent dispositions owing to the resiliency of the spring, whereby when the spring is implanted in the ear, the spring arms resist displacement of the spring towards the incision. The article is especially adapted for use as the implant in the implantation method in which a cannula-like sheath is inserted through the incision and into the pocket, so that the sheath bridges the fault, an elongated ear implant is inserted endwise in the sheath, and the sheath is removed from the pocket and from around the implant to deposit the implant in the ear in bridging relationship to the fault.

18 Claims, 14 Drawing Figures

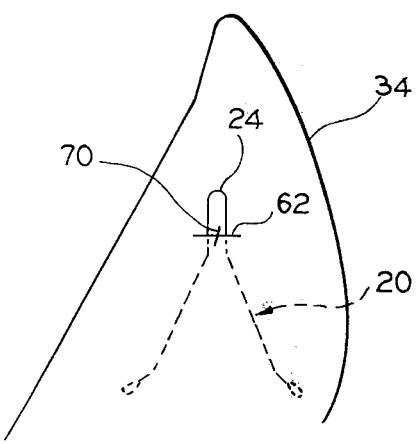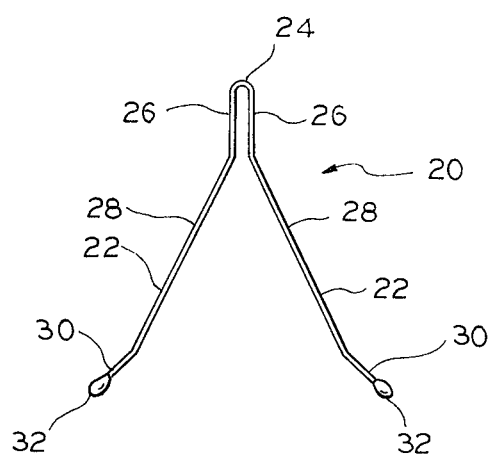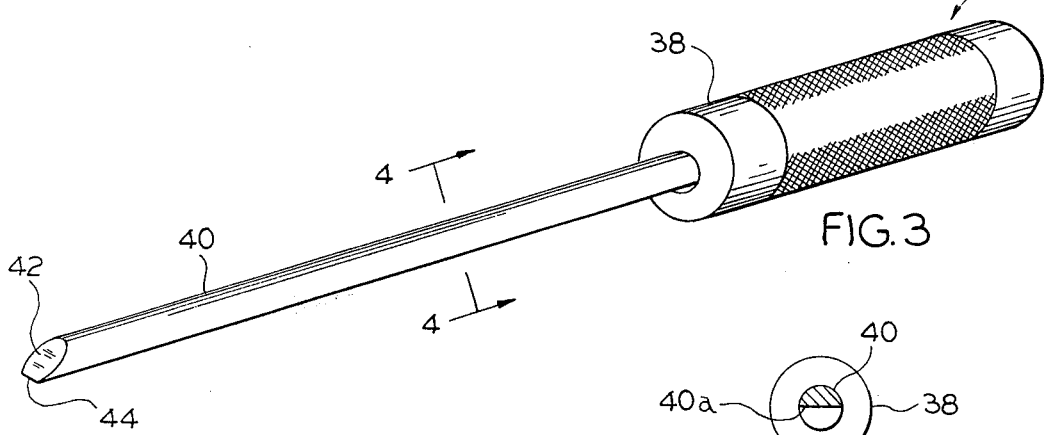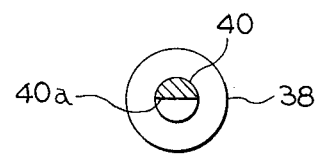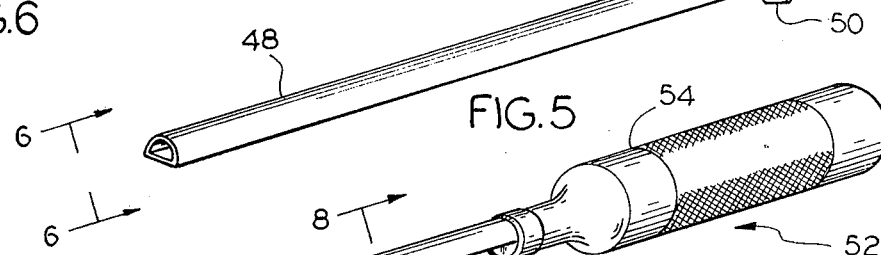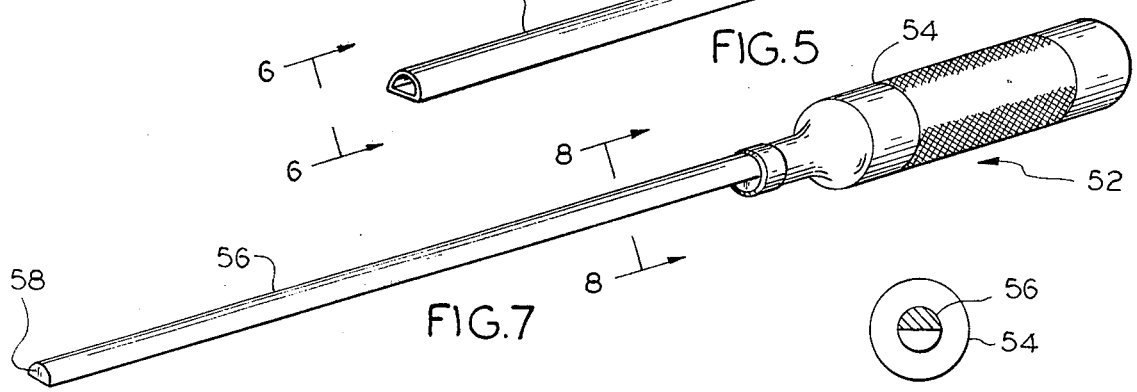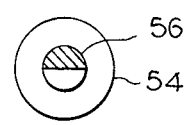

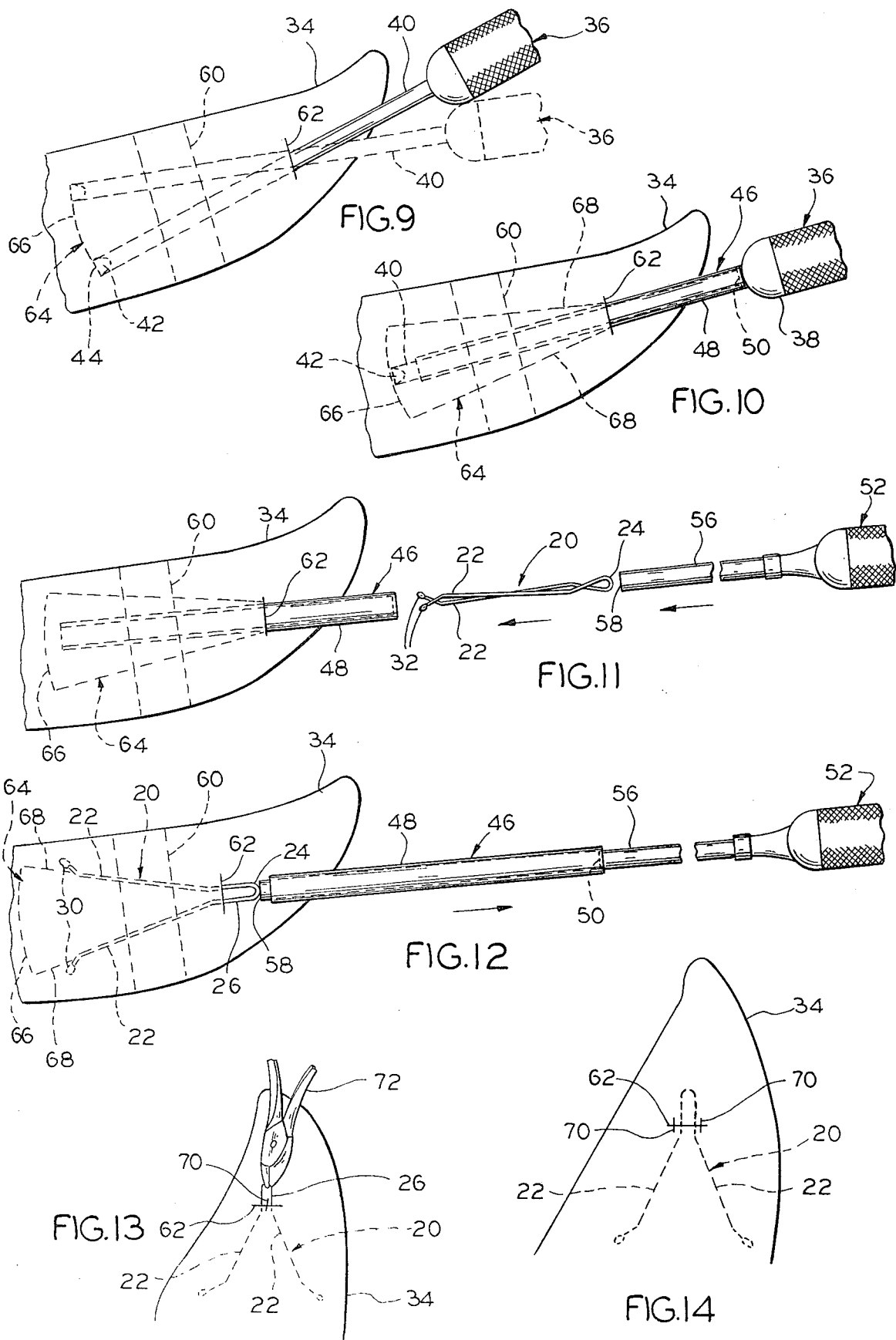

EAR IMPLANT ARTICLE AND IMPLANTATION METHOD

BACKGROUND OF THE INVENTION

This invention relates to an article of manufacture for use as an implant in the animal ear to correct a faulty carriage of the ear occasioned by the presence of a skin-enclosed cartilage fault, and to an implantation method employing the article.

Implants have been employed in the past to support weak or defective auricular cartilage in the animal ear, especially in the canine ear. The implants are used in cropped ears that fail to stand and in ears having damaged cartilage. In one technique, a surgical incision of substantial length is made in the skin along the length or longitudinally of the canine ear, across an area of weak or defective cartilage. The edges of the skin around the incision are spread apart so as to expose the cartilage over which an implant is to be laid, an elongated implant is put in place, and the skin overlying the implant is closed by suturing, after which an antibacterial dressing is applied and the ear is placed in a supporting bandage. A preferred implant material is porous polyethylene. Cartilage and tissue growth is stimulated, and such growth together with the implant provide sufficient rigidity to maintain an erect posture of the ear, with sufficient flexibility to retain the natural feel of the ear. The method and implant are disclosed in U.S. Pat. No. 4,010,494.

In my copending application Ser. No. 768,101, filed Feb. 14, 1977, now U.S. Pat. No. 4,147,164, I have disclosed and claimed an improved implantation method, wherein an elongated implant is inserted through a small or short incision in the skin of the ear, extending transversely of the ear, and into a pocket previously formed between the skin and cartilage over a cartilage fault, so that the implant bridges the fault. The insertion of the implant into the pocket is accomplished by first inserting a cannula-like sheath through the incision and into the pocket so that the sheath bridges the fault, thereafter inserting the implant endwise into the sheath, and removing the sheath from the pocket and from around the implant to deposit the implant in the ear in bridging relationship to the fault. The improved method has the advantages over the method dislosed in the above-identified patent, of reducing the required number of surgical steps, simplifying the closing of the incision, being more amenable to the maintenance of sterility, remarkedly reducing the number of sutures and requiring no internal absorbable sutures, and being performed in a substantially shorter period of time.

The porous polyethylene implant preferably employed prior to the present invention had a tendency to move under the skin under normal conditions of use, and at times would work out through the incision, the sutures being spread apart in the process. Also, abscessing occurred in a sizeable number of canine ears, due to foreign body reaction, and the implants worked out from beneath the skin where abscessed. The working out of an implant results especially from the dog shaking his head.

SUMMARY OF THE INVENTION

The present invention provides an article of manufacture for use as an implant in the animal ear, which markedly reduces the instances in which the implant works out or is worked out from beneath the skin. The article is constructed of biologically inert or non-reactive material, to eliminate foreign body reaction and abscessing caused thereby.

The implant article of the invention has the additional advantage that it is readily removed at any time after implantation, and need not remain in the ear permanently, although it may be permitted to do so. Therefore, when cell growth and tissue growth have been stimulated sufficiently to strengthen and/or repair weak, defective or damaged cartilage, the article may be removed, and no foreign body remains in the ear.

In particular, the invention provides an article of manufacture for use as an implant in the animal ear to correct a faulty carriage of the ear occasioned by the presence of a skin-enclosed cartilage fault, such article comprising a spring constructed of non-porous biologically inert material, the spring having outwardly divergent arms terminating in outer free ends and adapted to be forced together to present a narrow elongated spring outline for implantation of the spring in the ear by insertion through a small incision in the skin of the ear with the free ends foremost and into a pocket previously formed between the skin and cartilage over a cartilage fault, so that the spring bridges the fault, the spring arms when free of applied force tending to return to their original divergent dispositions owing to the resiliency of the spring, whereby when the spring is implanted in the ear, the spring arms resist displacement of the spring towards the incision.

The invention also provides an improvement in the implantation method in which a cannula-like sheath is inserted through a small incision in the skin of the ear and into a pocket formed between the skin and cartilage over the cartilage fault, so that the sheath bridges the fault, an elongated ear implant is inserted endwise in the thus-inserted sheath, and the sheath is removed from the pocket and from around the implant to deposit the implant in the ear in bridging relationship to the fault. Proceeding in accordance with the invention, the aforesaid article is employed as the implant in such method, with the above-described improvements in the results.

BRIEF DESCRIPTION OF THE DRAWINGS

The drawings illustrate a preferred construction of the new article of manufacture and use of the article in the improved implantation method, without limitation thereto. In the drawings, like elements are identified by like reference symbols in each of the views, and:

FIG. 1 is a schematic illustration of a portion of a canine ear having the article of the invention implanted therein in the most frequently employed manner;

FIG. 2 is an elevational view of a preferred embodiment of the article;

FIG. 3 is a perspective view of a trocar-like implement which may be employed to carry out the method;

FIG. 4 is a cross sectional view taken on line 4—4 of FIG. 3;

FIG. 5 is a perspective view of a cannula-like sheath which may be employed in carrying out the method;

FIG. 6 is a front end elevational view of the sheath, taken on line 6—6 of FIG. 5;

FIG. 7 is a perspective view of a thrust member which may be employed in carrying out the method;

FIG. 8 is a cross sectional view taken on line 8—8 of FIG. 7;

FIG. 9 is a schematic view of a portion of the canine ear having the implement of FIG. 3 inserted between the skin and cartilage thereof and manipulated, as indicated by full and broken lines, in the initial steps of the method;

FIG. 10 is a similar view, but illustrating a later step in the method, wherein the implement of FIG. 3 having the sheath of FIG. 5 carried thereby is inserted between the skin and cartilage of the ear;

FIG. 11 is a similar view, but illustrating the implement of FIG. 3 removed from the sheath of FIG. 5, which remains in the ear, and the introduction of the article of FIG. 2 into the sheath, with the assistance of the thrust member of FIG. 7;

FIG. 12 is a similar view, but illustrating the article in position in the ear and being held in place by the thrust member inserted through the sheath while the sheath is removed from the ear;

FIG. 13 illustrates a step in the subsequent removal of the article from the ear; and FIG. 14 is a view similar to FIG. 1, but illustrating an alternative manner of implantation, which is employed in certain instances.

DESCRIPTION OF THE PREFERRED EMBODIMENTS

Referring to the drawings, particularly to FIG. 2, a spring 20 constitutes a preferred embodiment of the article of the invnetion, used as an implant in the animal ear. The spring includes a pair of like arms 22 which diverge outwardly from a reverse bend 24 integral therewith. Each arm 22 includes an inner portion 26, which is integral with one end of the bend 24 and extends outwardly therefrom in closely adjacent but preferably at least partly spaced relation to the remaining inner portion 26. The integral bend 24 and inner arm portions 26 together form a generally U-shaped bight in the spring 20.

Each arm 22 includes an intermediate portion 28 having one end integral with the outer end of an inner portion 26 and extending outwardly therefrom at an obtuse angle. The intermediate portions 28 diverge outwardly therefrom at an acute angle.

Each arm 22 includes an outer portion 30 having one end integral with the outer end of an intermediate portion 28 and its opposite end terminating at or adjacent to an outer free end of the arm. Each outer portion 30 extends outwardly from the integral intermediate portion 28 at a preferably obtuse angle. The outer portions 30 diverge outwardly at an angle greater than the angle of divergence of the intermediate portions 28, and preferably at an obtuse angle of divergence.

Each arm 22 terminates in an enlarged blunt free end 32, which, in the preferred embodiment, is rounded and may be in a somewhat tear-drop shape.

The illustrative preferred spring 20 is constructed of stainless steel spring wire, by bending a length of the wire to form the bend 24 and the several arm portions 26, 28 and 30. The wire is biologically inert or non-reactive, non-porous and relatively thin or narrow. Preferably, the wire is of a type which is employed surgically for pinning bones and for other operations. A suitable commercially available wire is identified as Kirshner wire. The wire employed in making the illustrative article 20 has an exemplary diameter of about 0.05 inch.

Enlarged blunt free ends 32 may be provided on the ends of the outer arm portions 30 by the application of a droplet or small portion of stainless steel solder thereto, so as to provide the preferred rounded end or tip on each arm 22. In one manner of application, a small segment of each end of the wire may be bent back upon itself at the outer end of the corresponding portion 30, to serve as a small attachment loop holding the solder in place. Alternatively, other means and methods may be employed for providing blunt, preferably rounded ends on the arms 22, such as swaging or other metal working. The ends 32, like the spring wire, are non-porous and biologically inert.

The several dimensions and angles, and the wire size and spring strength employed in the article 20 are variables, which depend upon the size of the ear, and the condition to be corrected and its location. Preferred overall lengths for the article, measured from the bend 24 to the free ends 32, are in the range of about 1½ to 3 inches for use in the canine ear. The angle of divergence of the intermediate portions 28 in the illustrative embodiment is in the range of about 30°–60°, with the smaller angles generally being further preferred. The angle of divergence of the outer arm portions 30 in the illustrative embodiment preferably is about 90°–180°. The spring 20 may be supplied to users with the component portions thereof disposed at selected angles. The wire is adapted to being bent by the user, to increase or decrease any of the angles, as most desirable for use under the circumstances, and as described hereinafter.

The intermediate portions 28 constitute the major portions of the arms 22, and they provide longitudinal and lateral support for the ear, and means for extending the cartilage. The outward divergence of the intermediate portions 28 provides resistance to displacement of the spring 20 towards the incision through which the spring is inserted in the ear, as explained hereinafter. The greater divergence of the outer portions 30, causing such portions to extend more laterally in the ear, serves to better anchor the spring 20 against movement in any direction.

The enlarged blunt ends 32 protect against piercing the skin by the ends of the wires, and the rounded contour minimizes abrasion and irritation. The bight formed by the bend 24 and the inner arm portions 26 is a relatively narrow loop which may protrude through the narrow incision in the skin employed for introduction of the spring 20 as an implant. The space between the inner portions 26 affords room for suturing the skin between such portions.

The spring strength of the spring 20 is such as to enable the arms 22 to be forced together or compressed to present a narrow elongated spring outline, as illustrated in FIG. 11, for insertion of the spring through a small incision in the skin, and when free of applied force, tending to return the arms 22 to their original divergent dispositions. The spring arms 22 may be caused to bear laterally against the skin when the spring 20 is implanted, to resist displacement of the spring towards the incision and exert tension on the skin and cartilage between the arms.

The spring 20 when constructed of spring wire is especially well-adapted for use as an inert or non-reactive implant, as when formed of the preferred stainless steel. The wire and the blunt ends 32 provided thereon are non-porous and otherwise free of small openings, into which tissue might grow and interfere with later removal of the implant. Alternatively, springs similar to the spring 20 may be constructed of other resilient biologically inert or non-reactive materials, and provide advantages in accordance with the invention. For example, it is contemplated that a spring such as the spring 20 may be formed of a polysiloxane polymer or silicone rubber, such as products supplied under the trademark Silastic.

The spring 20 is implanted in an ear such as the canine ear 34 in a manner such as illustrated in FIGS. 1 and 14, employing the instruments illustrated in FIGS. 3-8 in the method disclosed in my aforesaid copending application, in a preferred embodiment of the improved method of the present invention. Referring to FIGS. 3 and 4, a trocar-like implement 36 includes a substantially cylindrical manipulating handle 38 and a shank 40 secured thereto. The shank 40 preferably is a solid bar constructed of stainless steel and semicircular in cross section. A bevel 42 extending at an illustrative angle of about 45° to the longitudinal axis of the shank 40 is provided at the forward or distal end of the shank, and the bevel preferably terminates in a sharp transverse cutting edge 44.

Referring to FIGS. 5 and 6, a cannula-like sheath 46 includes a semi-cylindrical tube 48 and a tab 50. The tube 48 fits closely over the implement shank 40. The tab 50 projects laterally from the proximal or rear end of the tube 48 and may be integral with the tube. The sheath 46 preferably is constructed of stainless steel.

Referring to FIGS. 7 and 8, a thrust member 52 includes a generally cylindrical handle 54 and an elongated shank 56 secured thereto. The shank 56 preferably is a solid bar constructed of stainless steel. The shank 56 has a semicircular cross section of the same diameter as the cross section of the implement shank 40, and terminates in a blunt distal end surface 58 perpendicular to its longitudinal axis. The thrust member shank 56 fits closely within the sheath tube 48, in the same manner as the implement shank 40, and the thrust member shank 56 is longer than the implement shank 40.

Referring to FIG. 9, the ear 34 is illustrated as having a transverse cartilage fault 60, schematically represented by broken lines. The fault may be a weak area or an area which has been injured in some manner. The ear is prepared for implantation by first making a short transverse incision 62 in the skin spaced from one side of the fault 60. The incision may be, for example, about ½ inch in length. The incision may be made on either side of the ear, and preferably is made on the inside of the ear. The incision may be made with the cutting edge 44 on the trocar-like implement 36, or by a surgical knife, as may be most convenient.

Thereafter, the implement shank 40 is inserted carefully through the incision 62, with the cutting edge 44 and the flat longitudinal surface 40a (FIG. 4) of the shank 40 adjacent to the cartilage. Insertion is continued, with the shank 40 separating the skin from the cartilage on both sides and over the fault 60, until the shank has reached a location spaced beyond the fault. At this time, the implement 36 is swung back and forth about a pivot point substantially at the slit 62, to separate the skin from the cartilage and form a pocket 64 which is generally traingular, more particularly, which substantially constitutes the sector of a circle. Referring to FIG. 10, the pocket 64 has a relatively wide inner end 66, formed at the end of the inserted shank 40, and sides 68 which converge from the inner end towards the slit 62. The sides 68 are defined by the opposte sides of the shank 40, respectively, as the implement 36 is swung or pivoted back and forth. The skin at the sides 68 is attached to the underlying cartilage.

In the preferred procedure, the pocket 64 is formed by the shank 40 of the implement 36 used alone, and the implement then is withdrawn from the pocket. The implement shank 40 next is inserted through the tube 48 of the sheath 46, with the tab 50 adjacent to the handle 38, as illustrated in FIG. 10. The resulting assembly of the implement 36 and the sheath 46 slidably mounted thereon is inserted through the incision 62 and into the pocket 64, with part of the sheath 46 projecting rearwardly out from the incision, also as illustrated in FIG. 10. The implement shank 40 and the sheath 46 thereon are inserted sufficiently so that the sheath bridges the fault 60, preferably by inserting the shank 40 to the inner end 66 of the pocket 64. The implement shank 40 next is withdrawn from the sheath 46 while the sheath is allowed to remain in the same position in the pocket 64, bridging the fault 60, as seen in FIG. 11.

With the sheath in the latter position, the arms 22 of the spring 20 are forced together, to present a narrow elongated spring outline, as illustrated in FIG. 11. This is done conveniently by finger pressure, the fingers being covered by a surgical glove. The compressed spring 20 is inserted in the sheath 46, using the fingers initially, with the free ends 32 of the spring foremost. Insertion using the fingers is followed by insertion by manipulation of the thrust member 52, causing the blunt distal end 58 of its shank 56 to abut against the rearwardly disposed bend 24 in the spring 20. In this manner, the spring 20 is inserted through the incision 62 and into the pocket 64 in bridging relationship to the fault 60, while encased in the sheath 46. The spring 20 is inserted readily in this manner, and no irritation or damage is caused by the insertion.

As illustrated in FIG. 12, the sheath 46 next is removed from the pocket 64 and from around the spring 20, by sliding the sheath 46 on the shank 56 of the thrust member 52 and completely out of the pocket. The tab 50 on the sheath may be grasped by the fingers for this purpose. At the same time, the thrust member 52 is held in place with its distal end 58 abuttingly engaging the rearwardly disposed bend 24 of the spring 20, to hold the spring in place bridging the fault 60, also as illustrated in FIG. 12.

As the sheath 46 is withdrawn from the pocket 64, freeing the spring arms 22, the resiliency of the spring 20 causes the spring arms to separate, and the arms tend to return to their original divergent dispositions. The spring arms 22 spread apart until they are caused to bear against the skin forming the sides 68 of the pocket 64, by the tension remaining in the spring, in the preferred procedure. The outer portions 30 of the arms 22 tend to penetrate further, between the skin and cartilage adjacent to the pocket 64, thereby anchoring the spring in place. As the sheath 46 is withdrawn, the skin forming the pocket 64 collapses on the spring 20, which bridges the fault 60. The divergence of the spring arms 22 and the force exerted by the arms against the skin bordering the pocket 64 provide resistance to removal or working out of the spring 20 from the ear through the incision 62, as the subject shakes its head or rubs its ear. The anchored outer portions 30 furnish resistance to movement of the spring 20 away from the incision 62.

In most cases, the implantation is intended to be temporary, and the bight portion of the spring 20 is allowed to protrude through the incision 62, as illustrated in FIGS. 1 and 12. The incision is closed between the inner spring arm portions 26 by a single stitch 70 (FIG. 1). This procedure is used with young dogs, for example, about 1-3 months of age, in connection with ear-trimming. The procedure also is used with most dogs having damaged or abnormal cartilage.

Temporary implantation as illustrated in FIGS. 1 and 12 is employed in young dogs having relatively long and floppy ears, such as Great Danes, Doberman Pinschers, Schnauzers, and Boxers, whose ears are trimmed and caused to stand up straight in this manner. The presence of the implanted spring 20 and the lateral tension imparted by the spring stimulate both cartilage development and tissue growth, which strengthen the ear so that it will remain upright. A period of about one to two weeks is required for the process to take place in young dogs. When the cartilage is damaged or abnormal, in the foregoing dogs or in dogs having ears which normally stand upright, including Scottish Terriers and German Shepherds, the implanted spring 20 is allowed to remain in the ear for a longer period of time, for about 1 to 6 months.

After the incision 62 is closed with the stitch 70 between the inner spring arm portions 26, as shown in FIG. 1, it is not necessary to dress or bandage the ear. The incision closes up rapidly around the protruding spring portions. When the time comes to remove the spring 20, it is cut through the bend 24 by a wire cutter 72, as illustrated in FIG. 13, and the arms 22 are pulled individually through the incision 62, to remove them from beneath the skin. The incision 62 heals completely thereafter.

In a small percentage of cases, implantation in full-grown dogs is intended to be permanent, and the spring 20 is inserted fully beneath the skin, as illustrated in FIG. 14. The procedure then is substantially the same as that described above with reference to FIGS. 9–12. In addition, the shank 40 of the implement 36 may be employed to loosen the skin for a short distance behind the incision 62, i.e., to the right in FIG. 9. After the spring 20 has been inserted as shown in FIG. 12, the projecting bight portion of the spring is tucked under the loose skin behind the incision 62. The incision 62 is sutured, employing two stitches 70, one on each side of the bight portion and adjacent thereto, as illustrated in FIG. 14. The incision 62 closes up rapidly thereafter, with no need for a dressing or bandage. Should it be desired to remove the permanently implanted spring 20 after healing takes place, an incision may be made in the skin for the purpose of exposing the bend 24, and the spring may be cut and withdrawn in the manner described above with reference to FIG. 13. The incision then may be sutured and allowed to heal.

The new article and method have proven to be very successful in avoiding the working out or excessive shifting of the article 20 after implantation, and with proper antisepsis, there is substantially no problem of abscessing. While the article and method are especially useful for correcting the carriage of the canine ear, it will be apparent that they may be employed similarly for correcting ear carriage in other lower animals or in humans. It will be apparent also that the article may be varied from the specific preferred spring 20 illustrative of the invention, while providing the advantages thereof. Likewise, the method steps may be varied from the specific steps illustrated and described, examples of suitable variations being disclosed in my above-identified copending application. It is intended that all such variations, changes and modifications be included within the scope of the appended claims.

Having thus described the invention, what I claim as new and desire to secure by Letters Patent is:

1. In a method of performing an implantation to correct a faulty carriage of the animal ear occasioned by the presence of a skin-enclosed cartilage fault, wherein a cannula-like sheath is inserted through a small incision in the skin of the ear and into a pocket formed between the skin and cartilage over said fault, so that the sheath bridges the fault, an elongated ear implant is inserted endwise in the thus-inserted sheath, and said sheath is removed from said pocket and from around said implant to deposit the implant in the ear in bridging relationship to the fault, the improvement which comprises employing as said implant a spring constructed of non-porous biologically inert material, said spring having two arms which include respective arm portions diverging outwardly from each other and which arms terminate in outer free ends, said arms being forcibly movable together to present a narrow elongated spring outline for endwise insertion in the sheath with said free ends foremost, said spring arms when free of applied force tending to return to the original divergent dispositions of said arm portions owing to the resiliency of the spring, whereby when the spring is implanted in the ear, the spring arms bear against the skin forming the sides of the pocket owing to tension remaining in the spring, thereby to exert tension on the skin and cartilage between the spring arms and to resist displacement of the spring towards the incision.

2. A method as defined in claim 1 and wherein said spring is constructed of stainless steel spring wire.

3. A method as defined in claim 1 and wherein said arms have enlarged blunt free ends.

4. A method as defined in claim 1 and wherein said arms include outwardly divergent first portions spaced inwardly from said free ends, and outwardly divergent second portions extending angularly outwardly from said first portions to said free ends at an angle of divergence greater than the angle of divergence of the first portions, said second portions tending to penetrate between the skin and the cartilage laterally adjacent to said pocket for anchoring the spring in place.

5. A method as defined in claim 4 and wherein said angle of divergence of said first portions is an acute angle, and said angle of divergence of said second portions is an obtuse angle.

6. A method as defined in claim 4 and wherein said arms have enlarged blunt free ends.

7. A method as defined in claim 4 and wherein said first portions extend outwardly from respective ends of a generally U-shaped bight in the article.

8. A method as defined in claim 7 and wherein said first and second portions and said bight are constructed integrally by bending a length of stainless steel spring wire.

9. In a method of performing an implantation to correct a faulty carriage of the animal ear occasioned by the presence of a skin-enclosed cartilage fault, wherein an elongated ear implant is inserted endwise through a small incision in the skin of the ear and into a pocket formed between the skin and cartilage over said fault, so that the implant bridges the fault, the improvement which comprises employing as said implant a spring constructed of non-porous biologically inert material, said spring having two arms which include respective arm portions diverging outwardly from each other and which arms terminate in outer free ends, said arms being forcibly movable together to present a narrow elongated spring outline for endwise insertion through said incision with said free ends foremost and into said pocket, said spring arms when free of applied force tending to return to the original divergent dispositions of said arm portions owing to the resiliency of the spring, whereby when the spring is implanted in the ear, the spring arms bear against the skin forming the sides of the pocket owing to tension remaining in the spring, thereby to exert tension on the skin and cartilage between the spring arms and to resist displacement of the spring toward the incision.

10. A method as defined in claim 9 and wherein said arms include outwardly divergent first portions spaced inwardly from said free ends, and outwardly divergent secnd portions extending angularly outwardly from said first portions to said free ends at an angle of divergence greater than the angle of divergence of the first portions, said second portions tending to penetrate between the skin and the cartilage laterally adjacent to said pocket for anchoring the spring in place.

11. A method as defined in claim 9 and wherein said arm portions extend outwardly from respective ends of a generally U-shaped bight in the article.

12. A method as defined in claim 11 and wherein said arm portions and said bight are constructed integrally by bending a length of spring wire.

13. In a combination of an animal ear implant article for correcting a faulty carriage of the ear occasioned by the presence of a skin-enclosed cartilage fault, a trocar-like implement for insertion through a small incision in the skin of the ear to form a pocket between the skin and cartilage over the cartilage fault, and a cannula-like sheath for insertion through said incision and into said pocket in bridging relationship to the cartilage fault, said sheath receiving said article endwise therein for insertion of the article into said pocket, and said sheath being removable from said pocket and from around said article to deposit the article in the ear in bridging relationship to the cartilage fault, the improvement wherein said article comprises a spring constructed of non-porous biologically inert material, said spring having two arms which include respective arm portions diverging outwardly from each other and which arms terminate in outer free ends, said arms being forcibly movable together to present a narrow elongated spring outline for insertion of the spring endwise into said sheath, said spring arms when free of applied force tending to return to the original divergent dispositions of said arm portions owing to the resiliency of the spring, whereby when the spring is deposited in the ear, the spring arms bear against the skin forming the sides of the pocket owing to tension remaining in the spring, thereby to exert tension on the skin and cartilage between the spring arms and to resist displacement of the spring towards the incision.

14. A combination as defined in claim 13 and wherein said arm portions extend outwardly from respective ends of a generally U-shaped bight in the article.

15. A combination as defined in claim 14 and wherein said arm portions and said bight are constructed integrally by bending a length of spring wire.

16. A combination as defined in claim 13 and wherein said arms include outwardly divergent first portions spaced inwardly from said free ends, and outwardly divergent second portions extending angularly outwardly from said first portions to said free ends at an angle of divergence greater than the angle of divergence of the first portions, whereby when the spring is deposited in the ear, said second portions tend to penetrate between the skin and the cartilage laterally adjacent to said pocket for anchoring the spring in place.

17. A combination as defined in claim 16 and wherein said angle of divergence of said first portions is an acute angle, and said angle of divergence of said second portions is an obtuse angle.

18. A combination as defined in claim 16 and wherein said first portions extend outwardly from respective ends of a generally U-shaped bight in the article.

* * * * *